(12) United States Patent
Swamy et al.

(10) Patent No.: US 9,853,587 B2
(45) Date of Patent: Dec. 26, 2017

(54) SYSTEM FOR OPERATING A THREE-PHASE VARIABLE FREQUENCY DRIVE FROM AN UNBALANCED THREE-PHASE OR SINGLE-PHASE AC SOURCE

(71) Applicant: Yaskawa America, Inc., Waukegan, IL (US)

(72) Inventors: Mahesh M. Swamy, Gurnee, IL (US); Anupama Balakrishnan, Waukegan, IL (US); Joshua David Collins, Urbana, MO (US)

(73) Assignee: Yaskawa America, Inc., Waukegan, IL (US)

( * ) Notice: Subject to any disclaimer, the term of this patent is extended or adjusted under 35 U.S.C. 154(b) by 521 days.

(21) Appl. No.: 14/259,385

(22) Filed: Apr. 23, 2014

(65) Prior Publication Data

US 2015/0311853 A1 Oct. 29, 2015

(51) Int. Cl.

| | | |
|---|---|---|
| H02P 1/00 | (2006.01) |
| H02P 1/28 | (2006.01) |
| H02P 3/00 | (2006.01) |
| H02P 7/06 | (2006.01) |
| H02P 7/14 | (2006.01) |
| H02P 23/00 | (2016.01) |
| H02P 25/00 | (2006.01) |
| H02P 27/00 | (2006.01) |
| H02P 27/04 | (2016.01) |
| H02M 1/15 | (2006.01) |
| H02M 5/458 | (2006.01) |
| H02M 7/5387 | (2007.01) |

(Continued)

(52) U.S. Cl.
CPC ............ *H02P 27/047* (2013.01); *H02M 1/15* (2013.01); *H02M 5/458* (2013.01); *H02M 7/53875* (2013.01); *A61B 17/1626* (2013.01); *B26B 19/00* (2013.01); *B26B 19/06* (2013.01); *B26B 19/38* (2013.01)

(58) Field of Classification Search
CPC ..... A61B 17/1626; B26B 19/00; B26B 19/06; B26B 19/38; B26B 19/388
USPC ........................................................ 318/504
See application file for complete search history.

(56) References Cited

U.S. PATENT DOCUMENTS

| | | | | |
|---|---|---|---|---|
| 4,137,489 A | * | 1/1979 | Lipo ....................... H02P 27/06 318/722 |
| 5,329,217 A | * | 7/1994 | Kerkman .......... H02M 7/53875 318/811 |

(Continued)

*Primary Examiner* — Shawki S Ismail
*Assistant Examiner* — Bradley Brown
(74) *Attorney, Agent, or Firm* — Wood, Phillips, Katz, Clark & Mortimer

(57) ABSTRACT

A variable frequency motor drive comprises a converter including a rectifier having an input for connection to an AC power source and converting the AC power to DC power. A DC bus is connected to the rectifier circuit. At least one bus capacitor is across the DC bus. An inverter receives DC power from the DC bus and converts the DC power to AC power to drive a motor. A controller is operatively connected to the converter. The controller comprises a speed control controlling the inverter responsive to a speed command to maintain a desired motor speed. A speed foldback control measures DC bus ripple voltage and regulates the speed command responsive to the measured DC bus ripple voltage.

20 Claims, 3 Drawing Sheets

(51) Int. Cl.
*B26B 19/06* (2006.01)
*A61B 17/16* (2006.01)
*B26B 19/00* (2006.01)
*B26B 19/38* (2006.01)

(56) References Cited

U.S. PATENT DOCUMENTS

| | | | |
|---|---|---|---|
| 2010/0229580 A1* | 9/2010 | Schnetzka | H02H 7/1216 62/228.4 |
| 2011/0025237 A1* | 2/2011 | Wystup | H02M 5/458 318/400.02 |
| 2011/0057588 A1* | 3/2011 | Rineh | H02P 3/18 318/380 |
| 2011/0234147 A1* | 9/2011 | Iwashita | B23Q 15/08 318/799 |
| 2012/0242273 A1* | 9/2012 | Hsieh | H02P 1/029 318/806 |
| 2014/0368143 A1* | 12/2014 | Breitzmann | H02P 3/22 318/400.22 |

* cited by examiner

SYSTEM FOR OPERATING A THREE-PHASE VARIABLE FREQUENCY DRIVE FROM AN UNBALANCED THREE-PHASE OR SINGLE-PHASE AC SOURCE

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD OF THE INVENTION

This invention relates to a motor drive system for operating a three-phase variable frequency drive from an unbalanced three-phase or single-phase AC source.

BACKGROUND

Motor drive systems using speed controls are in common usage and are successfully applied in many applications. A typical motor drive system uses an AC/DC converter connected via a DC bus to a DC/AC converter. The DC bus includes a DC bus filter capacitor. The motor drive system is controlled by a speed controller. Even though this configuration has proven reliable and durable, it suffers from the ripple current limitation of the DC bus filter capacitors. In the very act of performing its purpose as a filter, the capacitors conduct the AC portion of the rectified bus current directly across the converter. The ripple current flowing through the DC bus filter capacitors' internal resistance creates heat and raises the internal temperature of the capacitors reducing their life expectancy. Excessive ripple current can cause premature and catastrophic failure of the capacitors.

In many rural areas, due to unavailability of three-phase AC power, three-phase Variable Frequency Drives (VFDs) are often required to operate from single-phase AC source. To overcome this issue, many VFD manufacturers simply de-rate the drive. Since the RMS value of the input current when using a single-phase AC source is at least two times higher than with a three-phase AC source, there are certain issues that have to be addressed when using three-phase drives with single-phase AC source. Important issues while operating VFDs from single-phase AC source are input rectifier diode average and peak currents, capacitor heating due to higher ripple current, exceeding the current rating of input terminal blocks, etc. Depending on a particular drive, either one of the three factors mentioned above can be the weakest link. Hence the de-rate method needs to consider all three concurrently rather than just the DC bus voltage ripple as is presently practiced. Some of the traditional methods being used at present are discussed below.

Most of the concerns that arise when a single-phase AC supply is used to power up a three-phase motor drive system are generally addressed by severely de-rating the VFDs. The de-rating technique relies on the ripple current capacity of the DC bus capacitor in the VFD. Most electrolytic capacitor manufacturers provide 100 Hz or 120 Hz ripple handling capacity at a given temperature around the capacitor can. Using this information, most drive manufacturers calculate a single-phase power rating for the drive. This theoretical calculation is often verified by experimental tests to confirm that the core temperature of the capacitor does not exceed its rated value. A look up table for a variety of drive sizes is typically provided which the end users can refer to while de-rating the three-phase VFDs to operate from single-phase AC source.

In some cases where the VFD has a built-in DC link choke, the actual ripple current into the DC bus capacitor is naturally reduced and allows the VFD to handle a slightly higher load when powered from a single-phase AC source. Such options are made available by most drive manufacturers. Some drive manufacturers also suggest adding an input inductor of 0.01 pu~0.03 pu to reduce the capacitor ripple current to some extent.

In the frequency foldback method which is based on sensing the ripple voltage across the DC bus capacitors, as described in U.S. Pat. No. 7,330,779, the basic premise is that the DC bus ripple current amplitude can be predicted by measuring the ripple voltage across the DC bus capacitor. Since DC bus capacitor current cannot be directly measured, the '779 patent suggests using the DC bus capacitor voltage ripple, instead. The ripple across the DC bus voltage is measured and the output frequency of the drive is reduced accordingly to limit the output power and in the process limit the ripple current through the capacitor. Though this method in its various forms has been adopted in the industry, as shown in U.S. Pat. No. 6,244,825, and seems to limit the power rating of three-phase VFDs operating from single-phase AC source, it does not account for the stresses in other parts of the VFD, especially the rectifier diodes and the input terminals.

Traditional implementation of this method involves a simple proportional-integral (PI) control algorithm that has a ripple value set point based on the three-phase rating of the VFD and a simple look up table. The DC bus voltage is scanned periodically and the maximum and minimum values of the DC bus voltage during that period are used to calculate the ripple voltage. This value is used as the feedback in the ripple regulator PI loop. The set point is stored in a lookup table since it is predetermined based on the maximum allowable capacitor ripple current typically at 100 Hz~120 Hz and 60° C. for a given capacitor. If the measured DC bus ripple voltage feedback value exceeds the regulation level, the foldback function is triggered and the output speed is decreased. Decreasing the output frequency decreases the load on the VFD and limits the capacitor ripple current. It should be pointed out here that the capacitor ripple current is not directly measured. The DC bus capacitor voltage ripple is monitored and the capacitor ripple current is assumed to be directly proportional to it.

Though the frequency foldback based on DC bus voltage ripple method is simple and easy to use, certain issues have been observed in the field. The most important of all is that the DC bus capacitor ripple voltage tolerance level may be higher than the peak to peak current rippling handling capability of input diode rectifiers or the RMS current capacity of the input terminal blocks, especially in smaller sized VFDs. Hence, reducing the output frequency to only satisfy the ripple current rating of the DC bus capacitor may not be sufficient to limit the stresses in other components of the VFD.

Moreover, the bus ripple voltage foldback method is not a direct control method. The DC bus voltage ripple may not reflect the true state of the capacitor. If the capacitor has deteriorated in capacitance, the average voltage across it can be quite low while the ripple could still be within specified limits. A lower DC bus voltage will cause higher input current for a given load level and can adversely affect the input diodes and terminal blocks. Similar sequence of events can happen if the single-phase AC source feeding the drive is a weak AC source. The available DC bus voltage, due to a weak AC source can again be lower than normal and affect the output power being delivered by the drive. Hence, relying solely on the DC bus voltage ripple is not sufficient as it neglects external factors including input voltage, source impedance, effective capacitance, etc. that can affect the load level at which fold-back occurs, leading to poor utilization of the drive.

In some cases, even a three-phase AC source behaves like a quasi single-phase AC source as an imbalance in the system increases. This is typical of weak AC sources. Under light load condition, the AC source may appear to be fine but when the load increases, the weak AC system starts to behave abnormally and show imbalanced voltages such that the ripple in the DC bus and the peak diode current increase.

The present application is directed to improvements in operating a three-phase variable frequency drive from an unbalanced three-phase or single-phase AC source.

SUMMARY

When using three-phase Variable Frequency Drives (VFDs) with an unbalanced three-phase or a single-phase AC source, output power of the drive has to be limited to prevent higher component stresses in the drive and in the input power system. As described herein, output power may be limited by reducing the output frequency based on the average and/or ripple amplitude of the q-axis current.

In accordance with one aspect, there is disclosed a variable frequency motor drive comprising a converter including a rectifier having an input for connection to an AC power source and converting the AC power to DC power. A DC bus is connected to the rectifier circuit. At least one bus capacitor is across the DC bus. An inverter receives DC power from the DC bus and converts the DC power to AC power to drive a motor. A controller is operatively connected to the converter. The controller comprises a speed control controlling the converter responsive to a speed command to maintain a desired motor speed. A speed foldback control measures VFD output current and monitors a torque producing component of the VFD output current and regulates the speed command responsive to the torque producing component of the VFD output current.

In accordance with another aspect, the speed foldback control measures a q-axis component of VFD output current and regulates the speed command responsive to the q-axis component of the VFD output current.

It is a feature that the speed foldback control regulates the speed command responsive to an average of the q-axis component of the VFD output current.

It is another feature that the speed foldback control regulates the speed command responsive to a ripple value of the q-axis component of the VFD output current.

It is a further feature that the speed foldback control regulates the speed command responsive to both an average of and a ripple value of the q-axis component of the VFD output current. The speed foldback control may comprise a first proportional-integral control loop for regulating a maximum q-axis component of the VFD output current and a second proportional-integral control loop for regulating q-axis ripple current amplitude.

It is a further feature that the speed foldback control is adapted to determine which of the control loops has a higher priority select by adjusting levels in which each control loop is activated and actual regulation level for each of the control loops.

It is yet another feature that the rectifier input is connected to a single-phase AC power source.

There is disclosed in accordance with yet another aspect, a motor drive system comprising a diode rectifier receiving single-phase AC power from a source and converting the AC power to DC power. An inverter receives DC power and converts the DC power to AC power to drive a load. A DC bus is connected between the diode rectifier and the inverter to provide a relatively fixed DC voltage for the inverter. At least one bus capacitor is across the bus. A controller is operatively connected to the inverter. The controller comprises a speed control loop controlling the inverter responsive to a speed command to maintain a desired motor speed. A speed foldback control measures VFD output current and monitors a q-axis component of the VFD output current and regulates the speed command responsive to the q-axis component of the VFD output current.

Other features and advantages will be apparent from a review of the entire specification, including the appended claims and drawings.

DETAILED DESCRIPTION

Figures 1, 2:
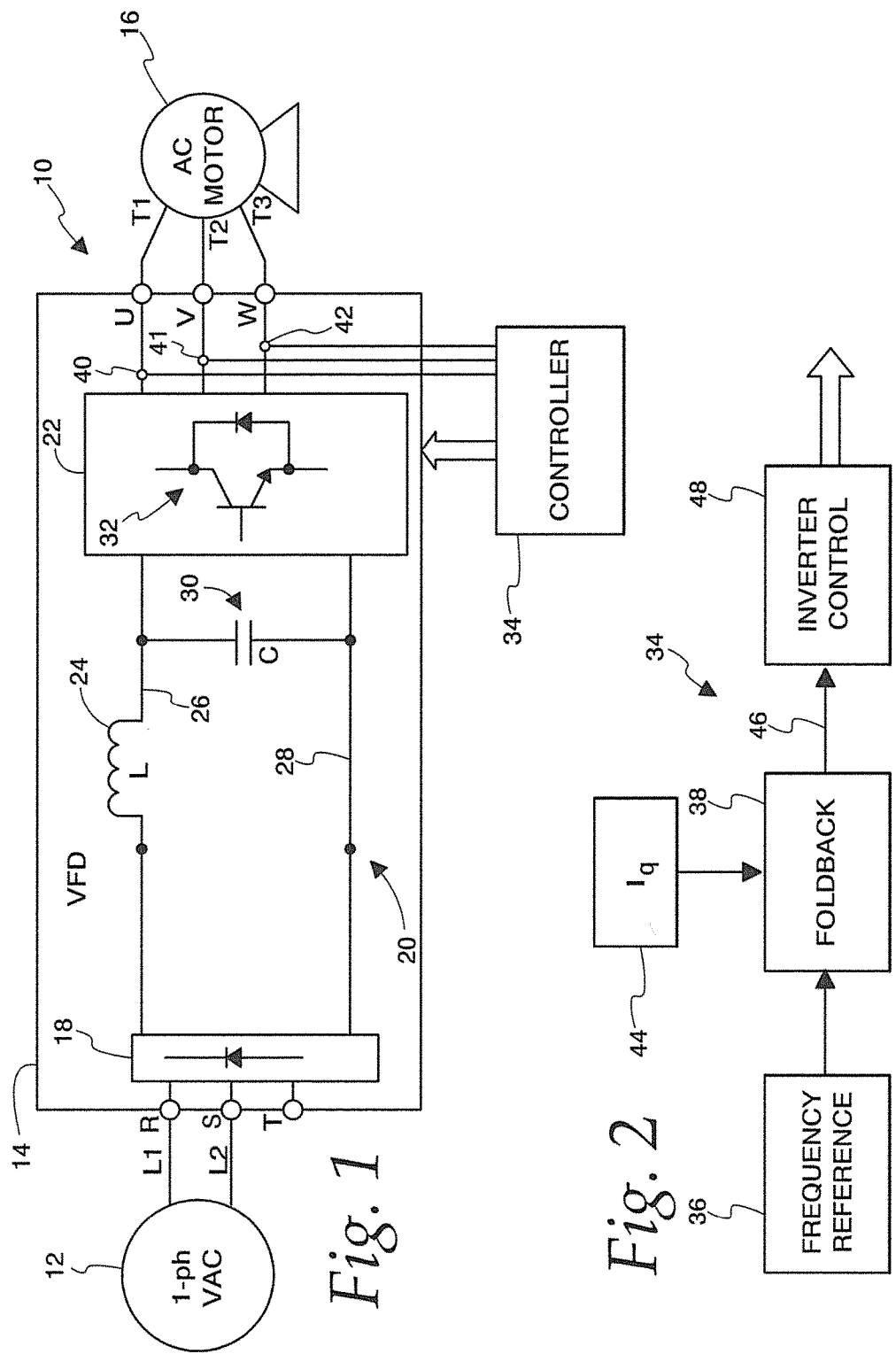
FIG. 1 is a schematic of a variable frequency motor drive.
FIG. 2 is a block diagram of the controller of FIG. 1.

Referring initially to FIG. 1, a motor drive system 10 is illustrated. The motor drive system 10 includes an AC source 12 powering a variable frequency drive (VFD) 14 for driving a motor 16. In the illustrated embodiment, the AC source 12 provides single-phase AC power on feeder conductors labeled L1 and L2 connected to respective terminals R and S the VFD 14. A terminal T, used with a three-phase source, is disconnected. As is apparent, the VFD 14 could be connected to a three-phase AC source using all three terminals R, S and T. The VFD 14, as described more particularly below, converts the AC power from the terminals R, S and T to DC power and converts it back to AC power at a select frequency which is then impressed across terminals U, V and W connected to motor terminals T1, T2 and T3, respectively.

The VFD 14 includes an AC/DC converter 18 connected by a DC bus 20 to a DC/AC converter 22. Particularly, according to the illustrated embodiment of the invention, the AC/DC converter 18 comprises a full wave bridge rectifier circuit of conventional construction which is operable to convert three-phase AC power to DC power. The DC bus 20 optionally includes a DC link choke 24. The DC link choke 24 reduces harmonics and ripple components. The DC bus 20 includes rails 26 and 28. A DC bus capacitor 30 is connected between the rails 26 and 28. As is known, there may be more than one DC bus capacitor. The DC/AC converter 22 comprises an inverter. Particularly, the inverter 22 comprises a pulse width modulation (PWM) inverter using insulated gate bipolar transistors (IGBTs) 32. Although not shown, six IGBTs 32 are connected in a three phase bridge configuration to the DC bus 20 to develop power at the terminals U, V and W, as is conventional. The IGBTs 32 are pulse width modulated using a controller 34, discussed below. Particularly, the PWM inverter 22 is controlled to create a sinusoidal effect for the motor 16. The pulse frequency used is fixed. The pulse width is varied to vary sinusoidal frequency.

More particularly, the PWM inverter 22 supplies a series of DC voltage pulses to the motor terminals U, V and W at a high frequency. The pulse width is varied so that the average voltage seen by the motor is a sine wave at a given frequency. Changing the width and frequency of the DC pulses varies the frequency of the voltage applied to the motor and thus the motor speed. The controller 34 is responsive to a frequency or speed reference to vary frequency of the voltage applied to the motor 16 to satisfy the desired frequency or speed reference, as is well known.

Referring to FIG. 2, a block diagram illustrates a portion of the controller 34 for implementing speed control. The controller 34 receives a frequency reference at a block 36. This reference may be generated through software or by look up table or the like, or be received from a remote device, as necessary or desired. The frequency reference is applied to a foldback control block 38 which regulates the frequency reference, and thus output power, based on average in ripple amplitude of the q-axis current to develop a speed command on a line 46. Particularly, the VFD 14 includes three current sensors 40, 41 and 42 which measure motor drive current. The sensed current values are supplied to the controller 34. The torque producing component or q-axis component of the sensed current values Iq is determined at a block 44 which is supplied to the foldback control block 38. The foldback control block 38 develops the speed command on the line 46 which is supplied to an inverter control block 48. The inverter control block 48 develops the switching signals for the inverter 22 in order to satisfy the speed command. Such converter control functionality is well known and is therefore not described further herein.

Figure 3:
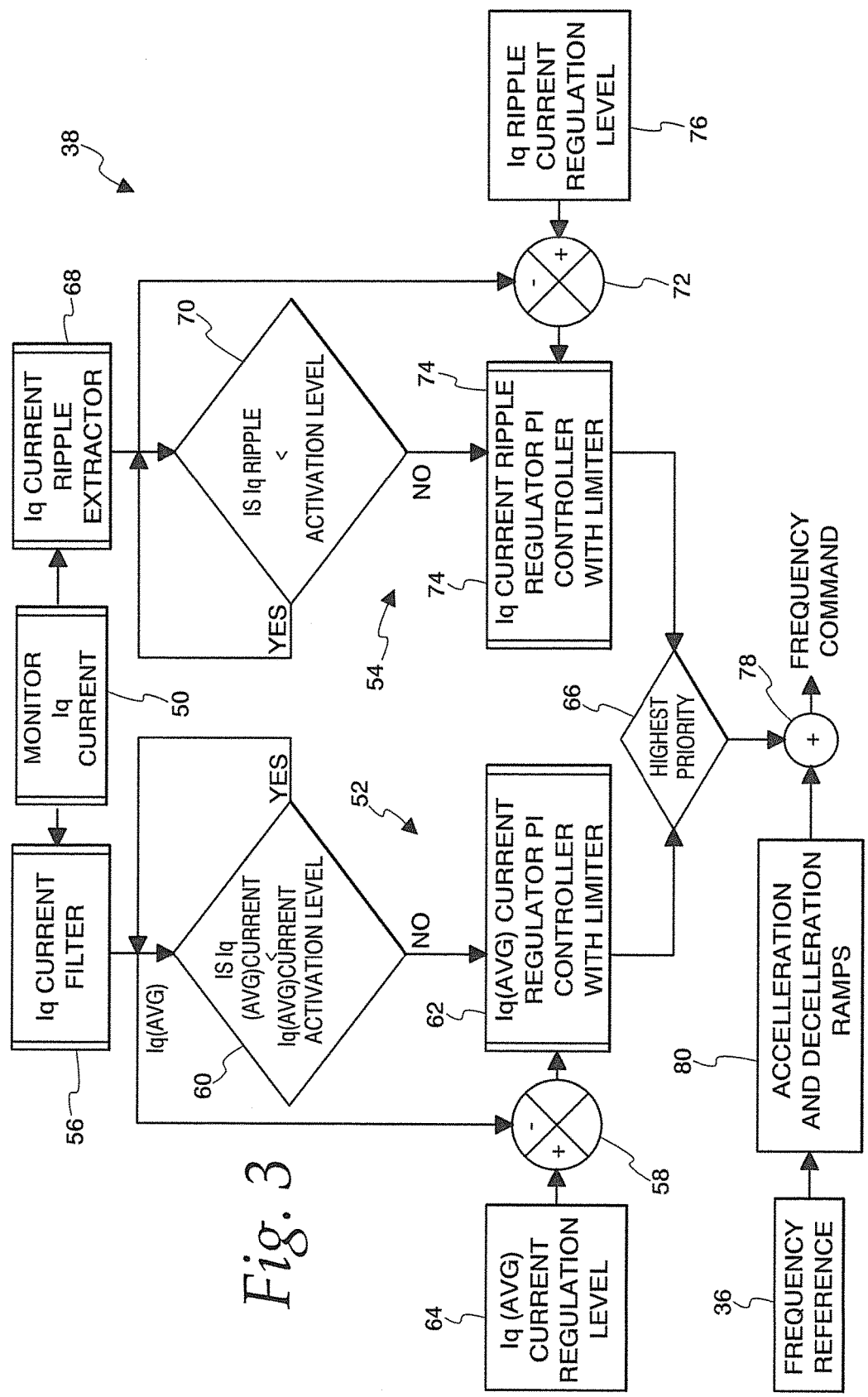
FIG. 3 is a flow diagram illustrating operation of a foldback algorithm implemented in the controller of FIG. 2.

Referring to FIG. 3, a flow diagram illustrates an algorithm for the foldback control in the block 38 of FIG. 2. The q-axis component of output current, from the block 44, is monitored at a block 50. The foldback control includes an average current loop 52 and a ripple current loop 54. Both received the q-axis current Iq monitored at the block 50.

The average current loop 52 includes a current filter 56 receiving the monitored current from the block 50 and determining an average of the q-axis current Iq. The average current value is supplied to a summer 58 and to a decision block 60. The decision block 60 determines if the average current value is less than a user defined preselect current activation level. If so, then the control loops back on the decision block 60. If not, then the control activates a block 62. A block 64 provides a user defined average current regulation level to the summer 58. The summer 58 determines the difference between the average current regulation level from the block 64 and the monitored average current from the filter 56 and supplies this as an input to the block 62. The block 62 comprises a first proportional-integral (PI) control loop for regulating a maximum of the q-axis average current value. The output of this control loop is supplied to a decision block 66.

The ripple control loop 54 includes a current ripple extractor block 68 which receives the q-axis component Iq of the output current and determines current ripple. This may be done, for example, by taking the maximum and minimum values of the sensed current. The ripple value is supplied to a decision block 70 and a summer 72. The decision block 70 determines if the ripple value is less than a user defined activation level. If so, then the control loops back around the block 70. If not, then the control activates a block 74. The block 74 comprises a second PI control loop for regulating q-axis ripple current amplitude. This is based on an input value from the second summer 72 which subtracts the ripple current value from the block 68 to a user defined ripple current regulation level from a block 76. The output of the second control loop in the block 74 is supplied to the decision block 66.

The decision block 66 determines which of the control loops 52 and 54 has a highest priority. This is selected by adjusting levels at which each control loop is activated and actual regulation level for each of the control loops. The output of the decision block 66 is supplied to a third summer 78. The frequency reference from the block 36, see FIG. 2, is supplied to an acceleration and deceleration ramp block 80 which provides conventional limiting functions on the frequency reference for start up and stopping and the like. The output from the block 80 is supplied to the summer 78 which varies the frequency reference from the block 36 based on the output from the highest priority of the two control loops 52 and 54 to determine the frequency or speed command which is output on the line 46, see FIG. 2, to the inverter control 48.

As described the method disclosed herein uses the q-axis current Iq flowing into the motor to regulate the maximum power that a drive can deliver when powered via a single-phase AC source without stressing the various components in the VFD 14. The details of the methodology are given below.

This methodology advocates the use of such a variable that has information of component stresses and is directly measured instead of estimated. The parameter that has information of load and stresses on drive components is the torque producing component of the output current. The output current from a VFD is directly measured on a continual basis for control and protection purposes in any VFD. The torque producing current is derived directly from the output current on a continual basis. Hence, choice of this directly measured output current component offers a controlled response to increase in load and hence increase in stresses in the components of a VFD, especially when it is powered from a single-phase AC source.

The torque producing current or the q-axis current Iq represents the active current of the motor and thus can accurately represent the capacitor ripple current as well as the input AC current flowing into the rectifier diodes. Further, the q-axis current includes the vagaries posed by external factors which affect the DC bus voltage as will be explained later. The q-axis current amplitude and ripple is also affected by the actual load on the drive at any given operating point. This allows for the frequency foldback control to respond to the increase in ripple current with load and hence achieve optimal utilization of the drive.

If there is reduction in average DC bus voltage due to deterioration of the capacitors in the DC bus or due to a weak AC system or due to imbalanced source voltage, and if more load is applied at the motor shaft, this immediately reflects in the q-axis current. Both the average value of q-axis current as well as the ripple value of the q-axis current increases. By regulating both the average and the ripple of the q-axis current, it is shown that the capacity of the VFD can be better optimized when it is powered from a single-phase AC source.

The control flow diagram for the foldback algorithm based on q-axis current has two PI controllers, as described relative to the blocks 62 and 74. The first controller 62 regulates the maximum output q-axis average current, which depends on the drive size and its voltage rating. The second controller 74 regulates the q-axis ripple current amplitude. The two controllers 62 and 74 work independently but, in general, the q-axis average current regulator has a higher priority. Depending on the relative rating of the repetitive peak diode current and the ripple current capacity of the DC bus capacitors, either the q-axis average current or the q-axis ripple current can be made to have a higher priority by adjusting the levels at which either controller is activated and the actual regulation level for each of these.

First, the q-axis average current control loop 52 is discussed. In this case, the drive's output q-axis average current is compared with the output q-axis average current activation level, at the block 60, set in a look-up table. If the measured value is higher than the activation level then the PI controller 62 of q-axis average current regulator is activated. The output of the PI controller 62 is negative and always subtracts from the frequency reference to generate a lower frequency command. If the output q-axis current is consistently higher than the regulation level, this PI regulator gradually saturates to the minimum output frequency, the value of which can be set by the user. Operating at the minimum speed for longer than a pre-programmed fixed amount of time will fault out the drive. However, if the load operates satisfactorily at the reduced frequency without demanding higher current, then the algorithm maintains an optimal frequency to regulate the output current at the set value.

Figure 5:
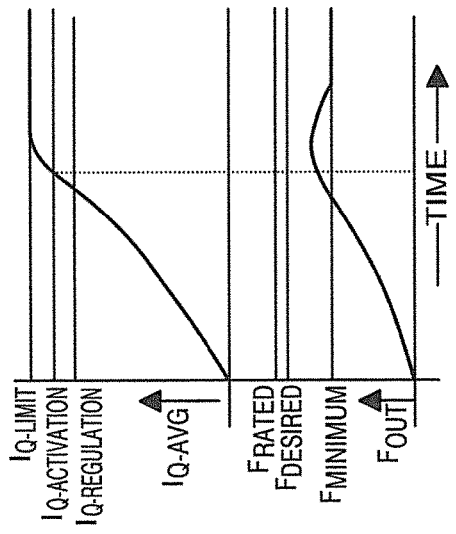
FIGS. 4-6 are curves illustrating operation of the speed foldback algorithm.
Figure 4:
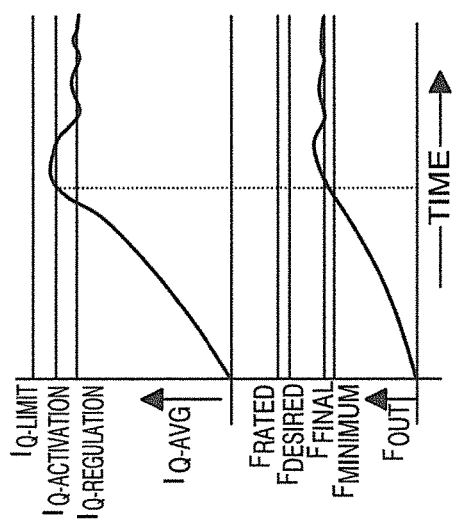

FIGS. 4 and 5 show a likely condition that requires regulating the q-axis current Iq. A typical operating sequence for a load profile where the load torque linearly increases with motor speed (representing a square law for power consumption) is shown. In FIG. 4, the output torque current regulator is shown to be activated, while in FIG. 5, the consequence of increasing the load torque close to the torque limit is shown to result in the drive operating at the user defined minimum operating speed. The Iq terms used in FIGS. 4 and 5 refer to average values.

The q-axis ripple current regulator loop 54 is discussed next. The q-axis ripple current amplitude is compared with the q-axis ripple current regulator activation level set in yet another look up table in the block 70. If the measured value is higher than the activation level then the ripple current regulator is activated and the PI controller 74 alters the output frequency such that the q-axis current ripple settles down to the regulation level. The output of the PI controller 74 is negative and always subtracts from the frequency reference to generate a lower frequency command. Once the ripple regulator is active, it can be deactivated only if the q-axis current ripple falls below the deactivation level. This ensures that the output of the PI controller 74 is operational only within the activation and deactivation levels thus preventing high output frequency swings that can result in high input diode peak current and high capacitor current.

Figure 6:
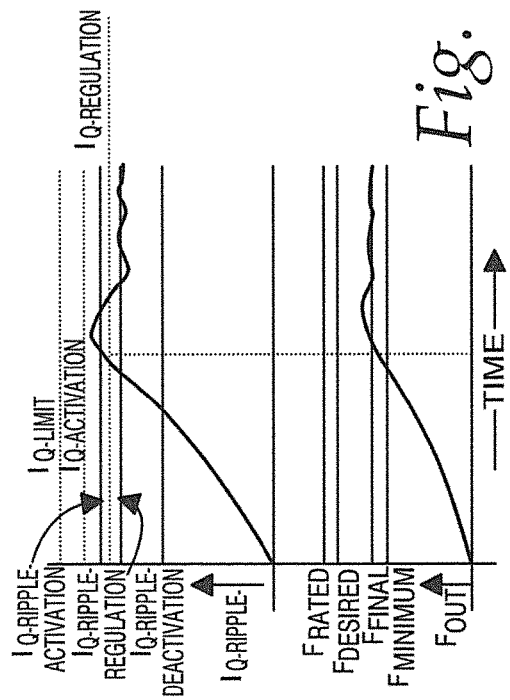

FIG. 6 shows a likely condition that illustrates the q-axis ripple current loop 54 in operation. Similar load profiles as that shown in FIGS. 4 and 5 are considered in FIG. 6. Here, the torque ripple is seen to increase, possibly due to single-phase operation. It is important to note that the average torque controller and the torque ripple controller act independently. However, in the example shown here, the average torque controller has a higher priority over the torque ripple controller and if the former is activated then the reduction in output frequency and hence torque is much faster and occurs with a more significant step size. For sake of comparison, the levels pertaining to the Iq average current controller (same as average output torque) are shown using dashed lines in FIG. 6.

As mentioned above, in some cases, even a three-phase AC source behaves like a quasi single-phase AC source as an imbalance in the system increases. This is typical of weak AC sources. Under light load conditions, the AC source may appear to be fine but when the load increases, the weak AC system starts to behave abnormally and show imbalanced voltages such that the ripple in the DC bus and the peak diode current increase. The q-axis current will also reflect this abnormal phenomenon and the VFD 14 can protect itself by folding back the output speed/frequency as discussed above.

By using the disclosed methodology, both the input peak current as well as the capacitor ripple current can be regulated, resulting in an optimal performance that limits the output power capacity of the drive to the rated single-phase value, without stressing any particular drive component beyond its rating. This offers direct control of the power drawn from the drive and thus allows for optimal utilization of the drive.

The disclosed system has been described with respect to flowcharts and block diagrams. It will be understood that each block of the flowchart and block diagrams can be implemented by computer program instructions. These program instructions may be provided to a processor to produce a machine, such that the instructions which execute on the processor create means for implementing the functions specified in the blocks. The computer program instructions may be executed by a processor to cause a series of operational steps to be performed by the processor to produce a computer implemented process such that the instructions which execute on the processor provide steps for implementing the functions specified in the blocks. Accordingly, the illustrations support combinations of means for performing a specified function and combinations of steps for performing the specified functions. It will also be understood that each block and combination of blocks can be implemented by special purpose hardware-based systems which perform the specified functions or steps, or combinations of special purpose hardware and computer instructions.

It will be appreciated by those skilled in the art that there are many possible modifications to be made to the specific forms of the features and components of the disclosed embodiments while keeping within the spirit of the concepts disclosed herein. Accordingly, no limitations to the specific forms of the embodiments disclosed herein should be read into the claims unless expressly recited in the claims. Although a few embodiments have been described in detail above, other modifications are possible. Other embodiments may be within the scope of the following claims.

The invention claimed is:

1. A variable frequency motor drive comprising:
 a converter including a rectifier having an input for connection to an AC power source and converting the AC power to DC power, a DC bus connected to the rectifier circuit, and at least one bus capacitor across the DC bus, and an inverter for receiving DC power from the DC bus and converting the DC power to AC power to drive a motor; and
 a controller operatively connected to the converter, the controller comprising a speed control controlling the inverter responsive to a speed command, and a speed foldback control measuring a torque producing component of VFD output current and folding back the speed command responsive to the torque producing component of the VFD output current exceeding a specified activation level.

2. The variable frequency motor drive of claim 1 wherein the speed fold back control folds back the speed command responsive to an average of the torque producing component of the VFD output current.

3. The variable frequency motor drive of claim 1 wherein the speed foldback control folds back the speed command responsive to a ripple value of the torque producing component of the VFD output current.

4. The variable frequency motor drive of claim 1 wherein the speed foldback control folds back the speed command responsive to both an average of and a ripple value of the q-axis component of the VFD output current.

5. The variable frequency motor drive of claim 4 wherein the speed foldback control comprises a first proportional-integral control loop for regulating a maximum q-axis component of the VFD output current and a second proportional-integral control loop for regulating q-axis ripple current amplitude.

6. The variable frequency motor drive of claim 5 wherein the speed foldback control is adapted to determine which of the control loops has a higher priority selected by adjusting levels at which each control loop is activated and actual regulation level for each of the control loops.

7. The variable frequency motor drive of claim 1 wherein the rectifier input is connected to a single-phase AC power source.

8. A variable frequency motor drive comprising:
a converter including a rectifier having an input for connection to an AC power source and converting the AC power to DC power, a DC bus connected to the rectifier circuit, and at least one bus capacitor across the DC bus, and an inverter for receiving DC power from the DC bus and converting the DC power to AC power to drive a motor; and
a controller operatively connected to the converter, the controller comprising a speed control controlling the inverter responsive to a speed command, and a speed foldback control measuring VFD output current and monitoring a q-axis component of the VFD output current and folding back the speed command responsive to the q-axis component of the VFD output current exceeding a specified activation level.

9. The variable frequency motor drive of claim 8 wherein the speed foldback control folds back the speed command responsive to an average of the q-axis component of the VFD output current.

10. The variable frequency motor drive of claim 8 wherein the speed foldback control folds back the speed command responsive to a ripple value of the q-axis component of the VFD output current.

11. The variable frequency motor drive of claim 8 wherein the speed foldback control folds back the speed command responsive to both an average of and a ripple value of the q-axis component of the VFD output current.

12. The variable frequency motor drive of claim 11 wherein the speed foldback control comprises a first proportional-integral control loop for regulating a maximum q-axis component of the VFD output current and a second proportional-integral control loop for regulating q-axis ripple current amplitude.

13. The variable frequency motor drive of claim 12 wherein the speed foldback control is adapted to determine which of the control loops has a higher priority selected by adjusting levels at which each control loop is activated and actual regulation level for each of the control loops.

14. The variable frequency motor drive of claim 8 wherein the rectifier input is connected to a single-phase AC power source.

15. A motor drive system comprising:
a diode rectifier receiving AC power from a source and converting the AC power to DC power;
an inverter for receiving DC power and converting the DC power to AC power to drive a load:
a DC bus connected between the diode rectifier and the inverter to provide a relatively fixed DC voltage for the inverter;
at least one bus capacitor across the bus; and
a controller operatively connected to the inverter, the controller comprising a speed control loop controlling the inverter responsive to a speed command, and a speed foldback control measuring VFD output current and monitoring a q-axis component of the VFD output current and folding back the speed command responsive to the q-axis component of the VFD output current exceeding a specified activation level.

16. The motor drive system of claim 15 wherein the speed foldback control folds back the speed command responsive to an average of the q-axis component of the VFD output current.

17. The motor drive system of claim 15 wherein the speed foldback control folds back the speed command responsive to a ripple value of the q-axis component of the VFD output current.

18. The motor drive system of claim 15 wherein the speed foldback control folds back the speed command responsive to both an average of and a ripple value of the q-axis component of the VFD output current.

19. The motor drive system of claim 18 wherein the speed foldback control comprises a first proportional-integral control loop for regulating a maximum q-axis component of the VFD output current and a second proportional-integral control loop for regulating q-axis ripple current amplitude.

20. The motor drive system of claim 19 wherein the speed foldback control is adapted to determine which of the control loops has a higher priority selected by adjusting levels at which each control loop is activated and actual regulation level for each of the control loops.

* * * * *